US006973718B2

(12) United States Patent
Sheppard, Jr. et al.

(10) Patent No.: US 6,973,718 B2
(45) Date of Patent: Dec. 13, 2005

(54) METHODS FOR CONFORMAL COATING AND SEALING MICROCHIP RESERVOIR DEVICES

(75) Inventors: Norman F. Sheppard, Jr., Bedford, MA (US); Christina M. Feakes, Brighton, MA (US)

(73) Assignee: MicroCHIPS, Inc., Bedford, MA (US)

( * ) Notice: Subject to any disclaimer, the term of this patent is extended or adjusted under 35 U.S.C. 154(b) by 130 days.

(21) Appl. No.: 10/158,811

(22) Filed: May 30, 2002

(65) Prior Publication Data

US 2002/0187260 A1     Dec. 12, 2002

Related U.S. Application Data

(60) Provisional application No. 60/294,462, filed on May 30, 2001.

(51) Int. Cl.[7] .............................. H05K 3/02; H05K 3/10
(52) U.S. Cl. ...................... 29/846; 29/841; 604/890.1; 604/93
(58) Field of Search ........................... 29/841, 842, 843

(56) References Cited

U.S. PATENT DOCUMENTS

| | | | |
|---|---|---|---|
| 4,146,029 A | 3/1979 | Ellinwood, Jr. |
| 4,345,981 A | 8/1982 | Bennett et al. |
| 4,360,019 A | 11/1982 | Portner et al. |
| 4,507,115 A | 3/1985 | Kambara et al. |
| 4,585,652 A | 4/1986 | Miller et al. |
| 4,731,051 A | 3/1988 | Fischell |
| 4,734,300 A | 3/1988 | Simanyi et al. |
| 4,793,825 A | 12/1988 | Benjamin et al. |
| 5,041,107 A | 8/1991 | Heil, Jr. |
| 5,067,491 A | 11/1991 | Taylor, II et al. |
| 5,167,625 A | 12/1992 | Jacobsen et al. |
| 5,170,801 A | 12/1992 | Casper et al. |
| 5,196,002 A | 3/1993 | Hanover et al. |
| 5,200,051 A | 4/1993 | Cozzette et al. |
| 5,252,294 A | 10/1993 | Kroy et al. |
| 5,288,504 A | 2/1994 | Versic |
| 5,304,293 A | 4/1994 | Tierney et al. |

(Continued)

FOREIGN PATENT DOCUMENTS

DE         197 16 683         6/1998

(Continued)

OTHER PUBLICATIONS

Armani, et al. "Microfabrication Technology for Polycaprolactone, a Biodegradable Polymer," J. Micromech. Microeng. 10 (2000) 80-84.

(Continued)

Primary Examiner—Richard Chang
(74) Attorney, Agent, or Firm—Sutherland Asbill & Brennan LLP

(57) ABSTRACT

Methods are provided for conformally coating microchip devices and for sealing reservoirs containing molecules or devices in a microchip device. One method comprises (i) providing a substrate having a plurality of reservoirs having reservoir openings in need of sealing; (ii) loading reservoir contents comprising molecules, a secondary device, or both, into the reservoirs; and (iii) applying a conformal coating barrier layer, such as a vapor depositable polymeric material, e.g., parylene, onto the reservoir contents over at least the reservoir openings to seal the reservoir openings. Another method comprises vapor depositing a conformal coating material onto a microchip device having at least two reservoirs and reservoir caps positioned over molecules or devices stored in the reservoirs, and providing that the conformal coating does not coat or is removed from the reservoir caps.

12 Claims, 5 Drawing Sheets

U.S. PATENT DOCUMENTS

| | | | | |
|---|---|---|---|---|
| 5,318,557 | A | 6/1994 | Gross | |
| 5,324,316 | A | 6/1994 | Schulman et al. | |
| 5,366,454 | A | 11/1994 | Currie et al. | |
| 5,368,588 | A | 11/1994 | Bettinger | |
| 5,368,704 | A | 11/1994 | Madou et al. | |
| 5,393,533 | A | 2/1995 | Versic | |
| 5,425,710 | A | 6/1995 | Khair et al. | |
| 5,443,508 | A | 8/1995 | Giampapa | |
| 5,510,138 | A | 4/1996 | Sanftleben et al. | |
| 5,524,338 | A | 6/1996 | Martyniuk et al. | |
| 5,562,715 | A | 10/1996 | Czura et al. | |
| 5,713,954 | A | 2/1998 | Rosenberg et al. | |
| 5,797,898 | A | 8/1998 | Santini, Jr. et al. | |
| 5,824,049 | A | 10/1998 | Ragheb et al. | |
| 5,893,974 | A | 4/1999 | Keller et al. | |
| 5,925,069 | A | 7/1999 | Graves et al. | |
| 5,938,923 | A | 8/1999 | Tu et al. | |
| 5,960,541 | A | * 10/1999 | Shea | 29/879 |
| 5,962,081 | A | 10/1999 | Öhman et al. | |
| 5,972,027 | A | 10/1999 | Johnson | |
| 5,989,445 | A | 11/1999 | Wise et al. | |
| 6,063,116 | A | 5/2000 | Kelleher | |
| 6,114,658 | A | 9/2000 | Roth et al. | |
| 6,123,861 | A | 9/2000 | Santini, Jr. et al. | |
| 6,136,212 | A | 10/2000 | Mastrangelo et al. | |
| 6,138,349 | A | * 10/2000 | Vinciarelli et al. | 29/841 |
| 6,243,608 | B1 | 6/2001 | Pauly et al. | |
| 2002/0072784 | A1 | 6/2002 | Sheppard, Jr. et al. | |
| 2002/0099359 | A1 | 7/2002 | Santini, Jr. et al. | |
| 2002/0119176 | A1 | 8/2002 | Greenberg et al. | |
| 2002/0138067 | A1 | 9/2002 | Sheppard, Jr. et al. | |

FOREIGN PATENT DOCUMENTS

| | | |
|---|---|---|
| WO | 01/12157 | 2/2001 |
| WO | 01/35928 | 5/2001 |
| WO | 01/41736 | 6/2001 |
| WO | 01/64344 | 9/2001 |
| WO | 01/91902 | 12/2001 |

OTHER PUBLICATIONS

Becker, et al. "Polymer Microfabrication Methods for Microfluidic Analytical Applications," Electrophoresis 2000, 21, 12-26.

Bremus-Kobberling, et al., "Laser Microperforation of a Retina Implant," Presentation at Microtechnology Conference, Germany, Sep. 25-26, 2000.

Cheng, et al. "Localized Silicon Fusion and Eutectic Bonding for MEMS Fabrication and Packaging," J. Microelectromechanical Systems, vol. 9, No. 1 (2000).

Low, et al., "Microactuators Towards Microvalves for Responsive Controlled Drug Delivery," Sensors & Actuators B 67: 149-60 (2000).

Madou & Florkey, "From Batch to Continuous Manufacturing of Microbiomedical Devices," Chem. Rev., 100: 2679-92 (2000).

Madou, Fundamentals of Microfabrication, pp. 468-512 (CRC Press 1997).

Madou & He, "Exploitation of a Novel Artificial Muscle for Controlled Drug Delivery," pp. 495-497 (1999).

Schwarz, et al., "Micro Implantable Visual Prostheses," 1st Annual Int'l IEEE-EMBS Special Topic Conference on Microtechnologies in Medicine & Biology, Lyon, France (Oct. 12-14, 2000).

Olson, "Parylene Conformal Coating and Its Application for Electronics," NOVA TRAN Parylene Coating Services, Proc. Int'l Electronics Packaging Conf., vol. 1 (Sep. 27, 1992).

Surbled, et al., "Array of Shape Memory Alloy One-Shot Micro-Valves for Drug Delivery", MME '99, Gif sur Yvette, France (Sep. 27-28, 1999).

Surbled, et al., "Shape Memory Alloys for Micromembranes Actuaction," SPIE. 3825: 63-70 (1999).

Yao, et al. "Low Temperature Eutectic Bonding for In-Plane Type Micro Thermoelectric Cooler," Proc. 2001 ASME Int'l Mechanical Engineering Congress & Exposition (Nov. 11-16, 2001).

* cited by examiner

METHODS FOR CONFORMAL COATING AND SEALING MICROCHIP RESERVOIR DEVICES

CROSS-REFERENCE TO RELATED APPLICATIONS

Priority is claimed under 35 U.S.C. §119 to U.S. provisional application Ser. No. 60/294,462, filed May 30, 2001.

BACKGROUND OF THE INVENTION

This invention is generally in the field of implantable miniaturized devices that provide controlled delivery or exposure of molecules or smaller devices. More specifically, the invention relates to implantable microchip devices.

When an implanted medical device such as a pacemaker is placed in the body, one needs to consider both the impact of the body on the device and the impact of the device on the body. The environment is electrically conductive and relatively corrosive, which can compromise the integrity and performance of the device electrically or mechanically. The presence of a foreign object in the body triggers the body's defense mechanisms, which can impair the functioning of the body and/or the device. One commonly used method to enhance the body's acceptance of the implanted device is coat the device with a biocompatible coating material.

Pinhole-free, conformal coatings are designed to seal devices from liquids and gases, while protecting and electrically insulating the device. Such coatings are typically used to conform to the surface contours of an assembled printed circuit board and electronic components. They protect the circuitry from the environment, prevent damage, provide mechanical strength, and increase dielectric strength between components. Examples of conformal coatings include silicone, urethane, acrylic, and epoxy. Typical methods for depositing these coatings include dipping, spraying, spin coating, and ultraviolet (UV) curing. U.S. Pat. No. 5,510,138 discloses a method of applying such coatings using hot melt dispensing equipment. Although these conformal coatings and processes are adequate for coating electronics and circuits, they may be inappropriate for microchip chemical delivery devices, such as described in U.S. Pat. Nos. 5,797,898 and 6,123,861 to Santini, Jr. et al. and in Nature, 397:335–38 (1999) and Angewandte Chemie, 39:2396–407 (2000). Most of the typical coatings require a high temperature or UV cure. Some are also solvent-based coatings, which could adversely react with the reservoir contents (e.g., drug molecules or a device) in the microchip device. These types of coatings also may be unacceptable due to trapped air bubbles and uneven coating.

Another coating material is parylene, which is used in numerous medical applications. Parylene is the common name of a family of vapor-deposited conformal coatings based on para-xylylene and its derivatives. U.S. Pat. Nos. 5,393,533 and 5,288,504 disclose the use of parylene in controlled release applications involving the encapsulation of drugs and cells for therapeutic applications. Catheters and other molded surgical devices can be parylene coated to protect the device against the corrosive effects of biofluids and can also aid in the release of these devices from the fabrication molds. U.S. Pat. No. 5,425,710 discloses using parylene coating to coat a sleeve of a dilation catheter balloon to protect it during insertion. As disclosed in U.S. Pat. No. 5,824,049, stents and prostheses can be parylene coated to protect them and allow cells to proliferate on them. Parylene provides corrosion resistance and electrical insulation on sensors implanted in the body without altering the device operation. U.S. Pat. No. 5,067,491 describes a blood pressure monitoring device coated in parylene to protect the sensor from the effects of the blood, ions, and water. Both the lumen and the outside of needles and probes can be coated with parylene to create a smooth surface. These needles may be used to make microelectrodes, as disclosed in U.S. Pat. No. 5,524,338. Implantable pacemakers and defibrillators can be sealed with parylene to protect and electrically insulate the devices.

One difficulty in using parylene to coat a microchip device would be that the reservoir caps over each reservoir of the completed microchip device must not be coated, in order for the device to operate. Therefore, the coating process would need to be followed by a selective removal process. Other types of implantable devices have a similar need to remove parylene from a portion of the device. For example, U.S. Pat. No. 5,925,069 (Sulzer Intermedics) discloses using a pulsed excimer laser to remove parylene coating from the surface of an implantable cardiac pulse generator to expose a defined region of the case to serve as an electrode. A UV-resistant mask or stencil between the device and the laser beam is used to create windows or openings in the parylene coating. This patent also discloses the use of plasma etching to remove parylene in patterns having defined shapes. In this process, the organic parylene reacts with the ionized oxygen plasma to form carbon dioxide gas and water vapor, which are removed by vacuum. A mask can create patterns of various shapes in the parylene by protecting certain areas from etching.

U.S. Pat. No. 5,562,715 discloses a silicone rubber or parylene coated pacemaker with detachable tabs that remove a portion of the coating and expose the electrodes. Windows in the parylene coating are patterned using a process that includes masking select surface areas of the device with tape, coating the entire surface of the device (masked and unmasked) with parylene, and then removing the tape to expose the select surface areas.

U.S. Pat. No. 4,734,300 discloses a process for the selective removal of parylene by contacting the areas of parylene to be removed with a chemical substance, such as tetrahydrofuran, to loosen the parylene coating so that it can be physically removed. A knife is used to score the parylene coating.

Such masking techniques may not be readily adaptable for masking individual tiny reservoir caps, which may, for example, be positioned in a closely packed array in a microchip device. For example, it may be difficult to create well-defined boundaries between coated and uncoated areas in very small microchip devices.

In one process of assembling microchip chemical delivery devices, it is necessary to seal the reservoir openings (distal the reservoir caps) after filling the reservoirs with the drug molecules or other reservoir contents. It would be advantageous to be able to seal the reservoir openings with a material that is compatible with the reservoir contents.

It would be desirable to provide microchip devices having a coating which enhances biocompatibility of the device and protects and insulates the device electronics, and which is compatible with the reservoir contents. It also would be desirable to provide a method of conformally coating a microchip device to seal the drug reservoirs, to electrically insulate the electrical connections, and to provide a biocompatible outer surface. It also would be desirable to provide microfabrication techniques for use in patterning a conformal coating on a microchip device so as to selectively pattern well-defined microscopic openings in the coating which correspond to the reservoir caps of the microchip device.

SUMMARY OF THE INVENTION

Microchip devices are provided with a conformal coating to give an inert and biocompatible surface for implantation of the microchip device, mitigating adverse responses by the body following implantation. In one embodiment, the microchip device for the controlled release or exposure of molecules or devices comprises: (1) a substrate having a plurality of reservoirs; (2) reservoir contents comprising molecules, a secondary device, or both, located in the reservoirs; (3) reservoir caps covering the reservoirs contents to isolate the reservoir contents from one or more environmental components outside the reservoirs; and (4) a conformal coating over the outer surface of at least a portion of the substrate other than the reservoir caps. The reservoir caps can be selectively disintegrated or permeabilized to expose the reservoir contents within selected reservoirs to the one or more environmental components. The conformal coating preferably comprises a vapor depositable polymeric material, such as parylene, which is biocompatible. In other embodiments, the biocompatible conformal coating includes acrylics, polyurethanes, silicones, or combinations thereof. The conformal coating has a thickness between 0.1 and 50 microns, preferably 10 microns. The conformal coating preferably covers all exterior surfaces of the device other than the reservoir caps. In one embodiment, the conformal coating is a laminate structure comprising two layers of parylene and a layer of a metal positioned therebetween.

In one embodiment, the reservoir contents comprise at least one therapeutic, prophylactic, or diagnostic agent. In another embodiment, the reservoir contents comprise a biosensor. The microchip device can include control circuitry to control the disintegration or permeabilization. It may further include a power source.

In another aspect, the microchip device includes a substrate having a front side and a back side, the back side comprising a plurality of reservoir openings distal the reservoir caps on the front side. The openings are sealed, at least in part, with a barrier layer comprising a conformal coating material. The openings can be further sealed with a mechanical or chemical sealing system secured over the barrier layer. The barrier layer also can be a laminate structure comprising two layers of parylene and a layer of a metal positioned therebetween.

Methods are provided for sealing reservoirs containing molecules or devices in a microchip device. The method can include (1) providing a substrate having a plurality of reservoirs, a front side, and a back side, the back side comprising a plurality of reservoir openings distal reservoir caps on the front side and in need of sealing; (2) loading reservoir contents comprising molecules, a secondary device, or both, into the reservoirs; and (3) applying a conformal coating barrier layer onto the reservoir contents over at least the reservoir openings to seal the reservoir openings. The conformal coating barrier layer can be applied by vapor deposition.

Methods are also provided for applying a conformal coating to a microchip device. The method can include (1) vapor depositing a conformal coating material onto a microchip device which comprises a substrate having a front side, a back side, and at least two reservoirs containing molecules or devices for selective release or exposure, and reservoir caps positioned on the front side of the substrate on each reservoir over the molecules or devices, wherein release or exposure of the molecules or devices from the reservoir is controlled by diffusion through or disintegration of the reservoir cap; and (2) providing that the conformal coating does not coat or is removed from the reservoir caps. In one embodiment, the reservoir caps are masked with a masking material before the vapor depositing step. In another embodiment, any coating material deposited onto the surface of the reservoir caps is subsequently removed, such as by chemical or plasma etching or by excimer laser.

DETAILED DESCRIPTION OF THE INVENTION

Figure 1:
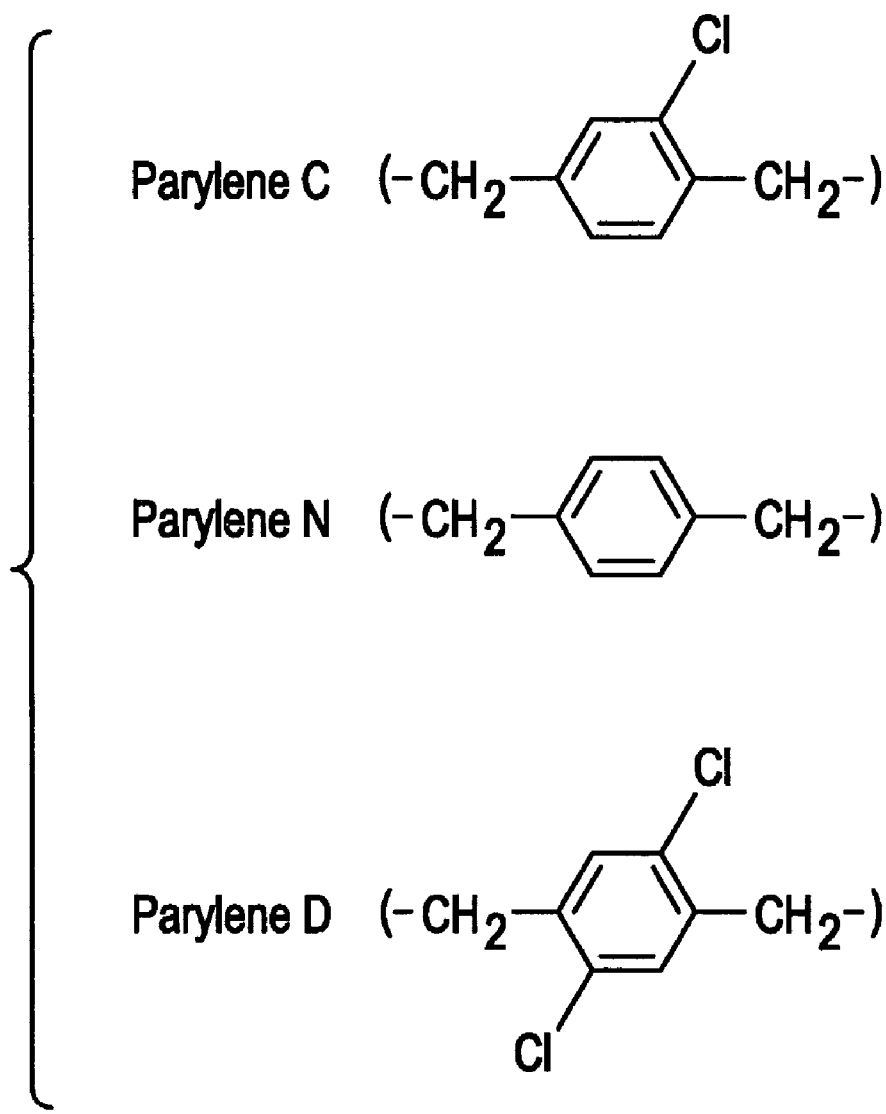
FIG. 1 depicts the chemical structures of Parylene C, Parylene N, and Parylene D.

Microchip devices having a conformal coating are provided that store and protect molecules and smaller devices from the environment for a period of time until controlled release or exposure of the molecules or smaller devices to the environment is desired. The microchip device includes (1) a substrate having a plurality of reservoirs; (2) reservoir contents comprising molecules, a secondary device, or both, located in the reservoirs; (3) reservoir caps covering the reservoirs contents to isolate said contents from one or more environmental components outside the reservoirs, wherein the reservoir caps can be selectively disintegrated or permeabilized to expose the reservoir contents within selected reservoirs to the one or more environmental components; and (4) a conformal coating over the outer surface of at least a portion of the substrate other than the reservoir caps. As used herein, the term "one or more environmental components" simply refers to constituents of the environment external the reservoirs, including, but not limited to, biological tissues and fluids at the site of implantation, air, fluids and particulates present during storage or in vitro use of the microchip devices.

The conformal coating preferably provides an inert and biocompatible surface for implantation of the microchip device, mitigating adverse responses by the body following implantation. The coating process desirably is one that avoids the need for solvents, heat, or chemical techniques that could degrade or damage the drug and/or device. For example, parylene can be deposited from a vapor preferably at room temperature and at a vacuum of approximately 0.1 torr. This is particularly advantageous for temperature sensitive drug molecules, which otherwise may be degraded by high temperature sealing or coating processes. The coating methods provide a means for containing and sealing a drug or other material in a microchip device, electrically insulating the electrical connections to the microchip, and at the same time provide an inert biocompatible coating suitable for implantation in the human body.

The microchip devices include a substrate having a plurality of reservoirs that contain the molecules or devices (i.e. the reservoir contents). The reservoirs can be individually filled and addressed, enabling the time and rate of release of multiple chemicals to be controlled. The reservoirs are closed at a first surface of the substrate by a reservoir cap or other membrane. Release or exposure of reservoir contents is from this first surface. The reservoirs also are closed at a second surface of the substrate distal the first surface. The reservoir opening at the second surface is sealed following filling of the reservoir with the reservoir contents. The conformal coating is applied either following or as part of the sealing process.

As used herein, a "microchip" is a miniaturized device fabricated using methods described in U.S. Pat. Nos. 5,797, 898 and 6,123,861, to Santini, Jr. et al., as well as other methods commonly applied to the manufacture of integrated circuits and MEMS (MicroElectroMechanical Systems) such as ultraviolet (UV) photolithography, reactive ion etching, and electron beam evaporation, as described, for example, by Wolf & Tauber, *Silicon Processing for the VLSI Era, Volume 1—Process Technology* (Lattice Press, Sunset Beach, Calif., 1986); and Jaeger, *Introduction to Microelectronic Fabrication*, Volume V in *The Modular Series on Solid State Devices* (Addison-Wesley, Reading, Mass., 1988), as well as MEMS methods that are not standard in making computer microchips, including those described, for example, in PCT WO 01/41736 and Madou, *Fundamentals of Microfabrication* (CRC Press, 1997), and other micromolding and micromachining and polymer forming techniques known in the art.

I. Device Components and Materials

The microchip devices include a substrate having a plurality of reservoirs, which contain the molecules or devices (i.e. the reservoir contents). The substrate, reservoirs, release system, reservoir caps, control circuitry and power source are substantially as described in U.S. Pat. Nos. 5,797,898 and 6,123,861, as well as PCT WO 02/30401, WO 02/30264, WO 01/91902, WO 01/64344, WO 01/41736, WO 01/35928, and WO 01/12157. A conformal coating is provided on select surfaces of the microchip device.

The Substrate

The substrate contains the reservoirs and serves as the support for the microchip. Any material which can serve as a support, which is suitable for etching or machining or which can be cast or molded, and which is impermeable to the contents of the reservoir and to the surrounding environment (e.g., water, blood, electrolytes, other solutions, or air) may be used as a substrate. Examples of suitable substrate materials include ceramics, glasses, certain metals, semiconductors, and degradable and non-degradable polymers. The substrate can be formed of only one material or can be a composite or multi-laminate material.

Conformal Coating

The material forming the conformal coating can be essentially any material or combination of materials that provide one or more, and preferably several, of the desired functions: strength, stability, biocompatibility, electrical insulation, moisture barrier properties, and processability (e.g., suitable parameters for application onto the microchip device). The material and application process desirably provides a uniform, bubble-free, pinhole-free coating. In a preferred embodiment, the conformal coating is provided over the entire surface of the microchip device with the exception of the reservoir caps.

The term "conformal" is used herein as known in the art, and refers to a coating designed to conform to the surface of the article being coating.

Parylene is the preferred conformal coating material. Parylene is the generic name for a family of poly(para-xylylene) polymers. There are a number of types of parylene, including Parylene N, Parylene C, and Parylene D. FIG. 1 shows the chemical structures for each of these three parylenes. They differ in the atomic substituents on the benzene ring of the xylylene molecule, which imparts different properties to the films, such as barrier protection, thermal stability, and lubricity. As used herein, the term "parylene" refers to any poly(para-xylylene) polymer or mixture thereof, unless a particular one is expressly indicated. Parylene is commercially available from such companies as Specialty Coating Systems (Indianapolis, Ind. USA) and Paratronix (Attleboro, Mass. USA).

Parylene is an effective coating as a moisture barrier. Parylene N absorbs 0.01% of water over 24 hours for a 0.019 inch (480 $\mu$m) thick coating, and Parylene C absorbs 0.06% of water over 24 hours for a 0.029 inch (740 $\mu$m) thick coating. Parylene N and Parylene C have also been tested and used in FDA approved implantable medical devices. These parylenes have been certified to comply with USP biological testing requirements for Class VI Plastics, which include Acute Systemic Toxicity, Irritation/Intracutaneous Reactivity, and Implantation.

Parylene is also an excellent electrical insulator. The short time dielectric strength of Parylene N is 7000 volts/mil ($2.8 \times 10^8$ V/m), Parylene C 6800 volts/mil ($2.7 \times 10^8$ V/m), and Parylene D 5500 volts/mil ($2.2 \times 10^8$ V/m), at 1 mil ($25 \times 10^6$ m).

The thickness of the parylene coating typically is between 0.1 microns and 50 microns or more. The particular thickness preferred depends upon the particular application and reservoir contents. As a general rule, the thicker the coating, the better the barrier properties of the coating. For example, the resistance to moisture transmission through the coating increases with increasing coating thickness. However, if one needs to define windows (i.e. open, uncoated areas) in the coating, for example to expose the reservoir caps, then that is more easily accomplished with a thinner coating. For example, making an accurate, 50 $\mu$m wide hole in a 10 $\mu$m thick film is easier than making the same hole in a 50 $\mu$m thick film. If the coating is too thin, however, pinholes may be formed in the film, unless the coating process is conducted in a cleanroom. In a preferred embodiment, the parylene coating thickness is about 10 $\mu$m.

Representative examples of other materials that may be suitable conformal coating materials include acrylics, polyurethanes, and silicones. Other vapor depositable, biocompatible, polymeric materials, including plasma-deposited polymer films, as well as materials having chemistries similar to that of parylene also can be used.

Conformal Coating Material as Barrier Layer

In an alternative embodiment, a vapor depositable conformal coating material, preferably parylene, is included as a barrier layer interposed between the reservoir contents and any other sealing material (to seal the opening used to fill the reservoirs—not to seal the reservoir cap side). In this embodiment, the conformal coating material can, but need not, coat the entire microchip device or device package. That is, the vapor depositable barrier layer material may coat the entire device or a portion thereof which includes the reservoir openings distal the reservoir caps.

The selected barrier layer desirably is compatible with the reservoir contents and generally would have little or no mixing with drug or other molecules in the reservoir. The coating material would be applied to form a solid or gel barrier layer. Following deposition of the barrier layer, any type of mechanical or chemical sealing system can be applied over or onto the barrier layer. Representative examples of mechanical sealing systems include the use of backing plates, such as described in PCT WO 01/91902. When a chemical sealing system is employed (e.g., epoxy), little or no mixing should occur at the interface of the barrier layer and chemical sealing system prior to cross-linking the sealing system.

Molecules and Secondary Devices (Reservoir Contents)

The reservoirs contain molecules, secondary devices, or combinations thereof, that need to be protected from surrounding environmental components until their release or exposure is desired. Proper functioning of certain reservoir contents, such as a catalyst or sensor, generally does not require their release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir.

Molecules

The reservoir contents can include essentially any natural or synthetic, organic or inorganic molecule or mixture thereof, for release (i.e. delivery) or retained and exposed. The molecules (i.e. chemicals) may be in pure solid, liquid, or gel form, or mixed with other materials that affect the release rate and/or time. Chemicals may be in the form of solid mixtures including, but not limited to, amorphous and crystalline mixed powders, monolithic solid mixtures, lyophilized powders, and solid interpenetrating networks; in the form of liquid mixtures including, but not limited to, solutions, emulsions, colloidal suspensions, and slurries; and in the form of gel mixtures including, but not limited to, hydrogels.

For in vivo applications, the chemical preferably is a therapeutic, prophylactic, or diagnostic agent. In one embodiment, the microchip device is used to deliver drugs systemically to a patient in need thereof. In another embodiment, the construction and placement of the microchip in a patient enables the local or regional release of drugs that may be too potent for systemic delivery of an effective dose. As used herein, "drugs" include any therapeutic, prophylactic or diagnostic agent, including organic or inorganic molecules, proteins, nucleic acids, polysaccharides and synthetic organic molecules, having a bioactive effect. Representative examples include analgesics, steroids, cytokines, psychotropic agents, chemotherapeutic agents, hormones, anesthetics, vaccines, metabolites, sugars, immunomodulators, antioxidants, ion channel regulators, and antibiotics. An example of a diagnostic agent is an imaging agent such as a contrast agent. The drugs can be in the form of a single drug or drug mixtures and can include pharmaceutically acceptable carriers.

In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures.

In another embodiment, the molecules to be released are perfumes, fragrances, dyes, coloring agents, sweeteners, or a variety of other compounds, which for example, may be useful to release as a function of temperature change.

In other embodiments, the reservoirs contain immobilized molecules. Examples include any chemical species which can be involved in a reaction, including, but not limited to, reagents; catalysts, including enzymes, metals, and zeolites; proteins; nucleic acids; polysaccharides; polymers; cells, as well as organic or inorganic molecules, including diagnostic agents.

Formulations of molecules to be released also may contain stabilizers and anti-oxidants to preserver the integrity of the drug or other molecules.

Secondary Devices

As used herein, unless explicitly indicated otherwise, the term "secondary device" includes, but is not limited to, any device and component thereof which can be located in or designed to operably communicate with one or more reservoirs in a microchip device. In a preferred embodiment, the secondary device is a sensor or sensing component. As used herein, a "sensing component" includes, but is not limited to, a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Secondary devices are further described in PCT WO 01/64344.

Examples of sensing components include components utilized in measuring or analyzing the presence, absence, or change in a drug, chemical, or ionic species, energy (or light), or one or more physical properties (e.g., pH, pressure) at a site. In a preferred embodiment, the microchip device is implantable in a patient (e.g., a human or other mammal) and includes sensors for monitoring the levels of glucose or urea in blood and other body fluids.

There are several different options for receiving and analyzing data obtained with devices located in the microchip devices. Typically, the operation of the microchip system will be controlled by an on-board (i.e. within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a microbattery or remotely by wireless transmission.

Reservoir Caps

As used herein, the "reservoir cap" includes a membrane, a reservoir cap, a plug, a thick or thin solid or semi-solid film, a two-phase interface (i.e. solid-liquid, liquid-liquid, or liquid-gas), or any other physical or chemical structure suitable for separating the contents of a reservoir from the environment outside of the reservoir. It generally is self-supporting across the reservoir opening. Selectively removing the reservoir cap or making it permeable will then "expose" the contents of the reservoir to the environment (or selected components thereof) surrounding the reservoir. In preferred embodiments, the barrier layer can be selectively disintegrated. As used herein, the term "disintegrate" is used broadly to include without limitation degrading, dissolving, rupturing, fracturing or some other form of mechanical failure, as well as a loss of structural integrity due to a chemical reaction or phase change, e.g., melting, in response to a change in temperature, unless a specific one of these mechanisms is indicated.

In passive devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor barrier layer materials include nanoporous or microporous silicon membranes.

In active devices, the reservoir cap includes any material that can be disintegrated or permeabilized in response to an applied stimulus (e.g., electric field or current, magnetic field, change in pH, or by thermal, chemical, electrochemical, or mechanical means). In a preferred embodiment, the reservoir cap is a thin metal membrane and is impermeable to the surrounding environment (e.g., body fluids or another chloride containing solution). Based on the type of metal and the surrounding environment, a particular electric potential is applied to the metal reservoir cap, which is then oxidized and disintegrated by an electrochemical reaction, to expose the contents of the reservoir to the surrounding environment. Examples of suitable reservoir cap materials include gold, silver, copper, and zinc. Any combination of passive or active barrier layers can be present in a single microchip device.

Device Packaging, Control Circuitry and Power Source

Active devices require actuation, which typically is done under the control of a microprocessor. The microprocessor is programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor.

Microelectronic device packages are typically made of an insulating or dielectric material such as aluminum oxide or silicon nitride. Low cost packages can also be made of plastics. Their purpose is to allow all components of the device to be placed in close proximity and to facilitate the interconnection of components to power sources and to each other, while protecting the electronics from the environment.

The control circuitry includes a microprocessor, a timer, a demultiplexer, and an input source (for example, a memory source, a signal receiver, or a biosensor), and a power source. The timer and demultiplexer circuitry can be designed and incorporated directly onto the surface of the microchip during electrode fabrication. The criteria for selection of a microprocessor are small size, low power requirement, and the ability to translate the output from memory sources, signal receivers, or biosensors into an address for the direction of power through the demultiplexer to a specific reservoir on the microchip device (see, e.g., Ji, et al., *IEEE J. Solid-State Circuits* 27:433–43 (1992)). Selection of a source of input to the microprocessor such as memory sources, signal receivers, or biosensors depends on the microchip device's particular application and whether device operation is preprogrammed, controlled by remote means, or controlled by feedback from its environment (i.e. biofeedback).

The criteria for selection of a power source are small size, sufficient power capacity, ability to be integrated with the control circuitry, the ability to be recharged, and the length of time before recharging is necessary. Batteries can be separately manufactured (i.e. off-the-shelf) or can be integrated with the microchip itself. Several lithium-based, rechargeable microbatteries are described in Jones & Akridge, "Development and performance of a rechargeable thin-film solid-state microbattery", *J. Power Sources*, 54:63–67 (1995); and Bates et al., "New amorphous thin-film lithium electrolyte and rechargeable microbattery", *IEEE 35$^{th}$ International Power Sources Symposium*, pp. 337–39 (1992). These batteries are typically only ten microns thick and occupy 1 $cm^2$ of area. One or more of these batteries can be incorporated directly onto the microchip device. Binyamin, et al., *J. Electrochem. Soc.*, 147: 2780–83 (2000) describes work directed toward development of biofuel cells, which if developed, may provide a low power source suitable for the operation of the microchip devices described herein, as well as other microelectronic devices, in vivo.

A microprocessor is used in conjunction with a source of memory such as programmable read only memory (PROM), a timer, a demultiplexer, and a power source such as a microbattery, as described, for example, by Jones et al. (1995) and Bates et al. (1992), or a biofuel cell, as described by Binyamin, et al. (2000). A programmed sequence of events including the time a reservoir is to be opened and the location or address of the reservoir is stored into the PROM by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

II. Methods of Making the Microchip Devices

The assembly of a complete microchip drug delivery device involves a number of packaging steps which may include (1) attachment of electrical leads to the microchip, (2) filling of the reservoirs with a chemical molecules or secondary devices for release or exposure, (3) sealing the reservoirs, (4) integration with electronic components and power sources, and (5) placing all microchips and components within a single enclosure or "package." For in vivo applications, this entire "package" must also be biocompatible. One possible assembly sequence might include filling the microchip, filling the reservoirs, attaching the electrical connections and leads, and sealing the entire package with a conformal coating.

Fabrication of the Substrates with Reservoirs

The microchip devices can be made using the methods described below, alone or in combination with known methods, such the microfabrication techniques described in U.S. Pat. Nos. 5,797,898 and 6,123,861, to Santini, et al. Other methods are described in PCT WO 01/41736. For example, the substrate can be formed from polymer, ceramic, or metal, e.g., by compression molding powders or slurries of polymer, ceramic, metal, or combinations thereof. Other forming methods useful with these materials include injection molding, thermoforming, casting, machining, and other methods known to those skilled in the art. Substrates formed using these methods can be formed (e.g., molded) to have the reservoirs or the reservoirs can be added in subsequent steps, such as by etching.

Fabrication of Reservoir Caps

In the fabrication of passive microchip devices, the reservoir cap material preferably is injected with a micro-syringe, printed with an inkjet printer cartridge, or spin coated into a reservoir having the thin membrane of insulating mask material still present over the small opening of the reservoir. If injection or inkjet printing methods are used, reservoir cap formation is complete after the material is injected or printed into the reservoir and does not require further processing. If spin coating is used, the reservoir cap material is planarized by multiple spin coatings. The surface of the film is then etched by a plasma, ion beam, or chemical etchant until the desired reservoir cap thickness is obtained. After deposition of the reservoir cap material, and possibly after reservoir filling, the insulating mask material is removed, typically via dry or wet etching techniques. It is understood that each reservoir also can be capped individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

In active devices, the reservoir cap and related circuitry can be deposited, patterned, and etched using microelectronic and MEMS fabrication methods well known to those skilled in the art, reviewed, for example, by Wolf et al. (1986), Jaeger (1988), and Madou, *Fundamentals of Microfabrication* (CRC Press, 1997). The reservoir cap and associated circuitry also can be formed on the surface of microchip devices using microcontact printing and soft lithography methods, as described, for example, in Yan, et al., *J. Amer. Chem. Soc.*, 120:6179–80 (1998); Xia, et al., *Adv. Mater.*, 8(12):1015–17 (1996); Gorman, et al., *Chem. Mater.*, 7:52–59 (1995); Xia, et al., *Annu. Rev. Mater. Sci.*, 28:153–84 (1998); and Xia, et al., *Angew. Chem. Int. Ed.*, 37:550–75 (1998). In a preferred embodiment, the barrier layer is defined using a lift-off technique. Briefly, photoresist is patterned in the form of electrodes on the surface of the substrate having the reservoirs covered by the thin membrane of insulating or dielectric material. The photoresist is developed such that the area directly over the covered opening of the reservoir is left uncovered by photoresist and is in the shape of an anode. A thin film of conductive material capable of dissolving into solution or forming soluble ions or oxidation compounds upon the application of an electric potential is deposited over the entire surface using deposition techniques such as chemical vapor deposition, electron or ion beam evaporation, sputtering, spin coating, and other techniques known in the art. Exemplary materials include metals such as copper, gold, silver, and zinc and some polymers, as disclosed by Kwon et al. (1991) and Bae et al. (1994). After film deposition, the photoresist is stripped from the substrate. This removes the deposited film, except in those areas not covered by photoresist, which leaves conducting material on the surface of the substrate in the form of electrodes. The anode serves as the active reservoir cap and the placement of the cathodes on the device is dependent upon the device's application and method of electric potential control. The electrodes are positioned in such a way that when a suitable electric potential is applied between an anode and a cathode, the unprotected (not covered by dielectric) portion of the anode barrier layer oxidizes to form soluble compounds or ions that disintegrate into solution, compromising the barrier separating the reservoir contents from the surrounding environment.

Reservoir Filling

The chemicals and devices to be stored and protected within the reservoirs are inserted into one of the openings of each reservoir (e.g., the large opening of square pyramid-shaped reservoirs). Chemicals can be inserted into the reservoir by injection, inkjet printing, or spin coating. Devices or device components can be fabricated inside or near each reservoir, or can be fabricated away from the microchip and inserted into or placed near a reservoir during microchip and packaging assembly. Each reservoir can contain different chemicals, devices, or device components. It is understood that each reservoir can be filled individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques. Each reservoir can also contain a different device or device component. Such devices can be fabricated directly in each reservoir. In one embodiment, thin metal electrodes for use in a sensing application can be fabricated onto the sidewalls of a pyramid-shaped reservoir using photolithography and electron beam evaporation.

Device Packaging, Control Circuitry, and Power Source

The manufacture, size, and location of the power source, microprocessor, PROM, timer, demultiplexer, and other components are dependent upon the requirements of a particular application. In a preferred embodiment, the memory, timer, microprocessor, and demultiplexer circuitry is integrated directly onto the surface of the microchip. The microbattery is attached to the other side of the microchip and is connected to the device circuitry by vias or thin wires. However, in some cases, it is possible to use separate, prefabricated, component chips for memory, timing, processing, and demultiplexing. In a preferred embodiment, these components are attached to the back side of the microchip device with the battery. In another preferred embodiment, the component chips and battery are placed on the front of or next to the microchip device, for example similar to how it is done in multi-chip modules (MCMs) and hybrid circuit packages. The size and type of prefabricated chips used depends on the overall dimensions of the microchip device and the number of reservoirs, and the complexity of the control required for the application.

Coating and Sealing the Microchip Devices

The openings through which the reservoirs of the devices are filled generally must subsequently be sealed. This sealing can be by mechanically or chemically securing a backplate over the openings. Alternatively, the opening can be sealed by applying a fluid material (e.g., an adhesive such as epoxy, a wax, or a polymer) that plugs the opening and hardens to form a seal that is impervious to the surrounding environment. Following this sealing process, a separate conformal coating can be applied. In an alternative embodiment, the conformal coating is used in place of a separate sealing step, such that the conformal coating is used to seal the reservoir openings and provide the biocompatible coating surface over the entire microchip device package.

In one embodiment, after electrical connections have been made in the circuitry (e.g., for providing the electrical potential means for disintegrating each reservoir cap), the reservoirs are ready to be filled with drug molecules. The conformal coating can then be applied directly onto the substrate and filled reservoirs, or alternatively, an intermediate coating, such as a wax layer, may be deposited after drug filling and before parylene coating in order to enhance reservoir sealing or eliminate trapped air pockets. In another embodiment, the barrier properties of the sealing layer can be improved by vapor depositing a layer of parylene over the open ends of the filled reservoirs. A metal layer is then sputtered or evaporated over the first parylene layer. Finally, another layer of parylene is deposited over the metal layer to give a biocompatible outer surface.

(a). Conformal Coating Process

Known conformal coating processes can be selected and used based, at least in part, on the coating material and any process limitations of the microchip device (e.g., temperature limitations of the reservoir contents).

Depending on the conformal coating process, it may be advantageous to chemically treat, or prime, the surfaces of the microchip device so as to improve the adhesion of the conformal coating. The family of materials known as silane adhesion promoters may be used on the silicon surfaces of the microchip device, and specific silanes, such as gamma-aminopropyltriethoxy silane, are often used for glass and silicon dioxide surfaces. The adhesion promoter may need to be applied before the reservoir contents are loaded into the microchip to prevent the drug molecules or other contents from being exposed to the silane. Substrates formed of materials other than silicon can be primed with other known adhesion promoters suitable for the particular substrate/conformal coating material selected.

Figure 2:
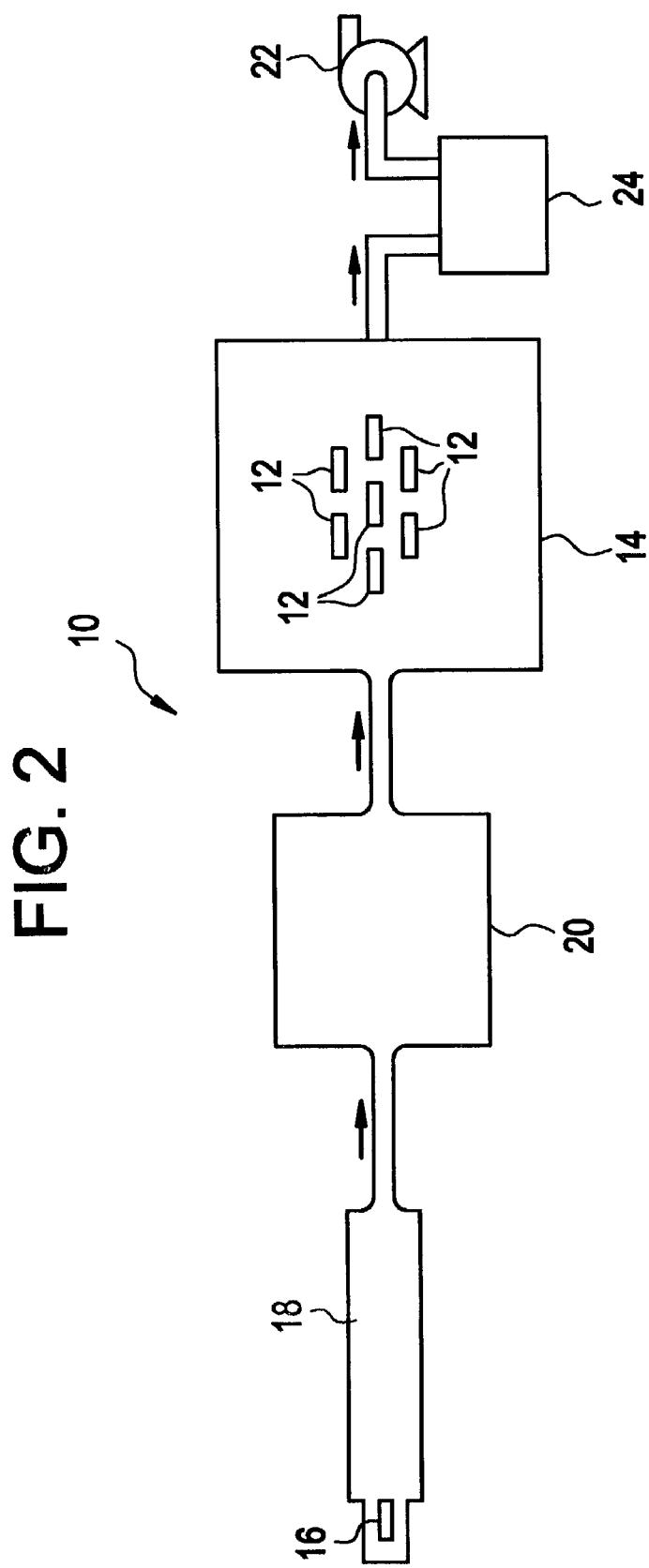
FIG. 2 is a process flow diagram illustrating one embodiment of a parylene conformal coating process.

One embodiment of a parylene deposition system 10 is shown in FIG. 2. To conformally coat the microchip devices (alone or with a carrier and associated leads) 12 with parylene, the assembled devices 12 are placed in a deposition chamber 14 of the parylene deposition system at room temperature. The source of parylene, the parylene dimer 16, is placed in a sublimation chamber (or vaporizer) 18 at the opposite end of the deposition system. The thickness of the parylene coating is determined by the volume of the dimer placed in the chamber. The dimer is heated, for example to about 175° C., in the sublimation chamber to cause it to sublimate. A pyrolysis tube 20 is located in fluid communication between the deposition chamber and the sublimation chamber. The deposition chamber 14 is held at a slight vacuum, for example with vacuum pump 22, so the pressure difference between the chambers moves the vaporized parylene dimer molecules through the pyrolysis tube 20. Exemplary values could be 1 torr in the sublimation chamber, 0.5 torr in the pyrolysis tube, and 0.1 torr in the deposition chamber. In the pyrolysis tube 20, the parylene dimer is then heated, for example to about 680° C., to cause it to cleave into two radical monomers. These monomer molecules enter the deposition chamber 14 and coat all the surfaces within the chamber, including the assembled microchip devices 12. A cold trap 24 collects any parylene flowing to the vacuum pump. This process also can be adapted to vapor deposit polymers other than parylenes, but which may have chemistries similar to that of parylenes.

It may be desired to increase the barrier properties of the parylene or other coating material by making a multi-laminate coating. In a preferred embodiment, a metal film, such as aluminum, is evaporated or sputtered onto a first layer of parylene. Another layer of parylene is then deposited onto the metal layer to maintain the biocompatibility of the multi-laminate film. In this embodiment, the first layer of parylene electrically insulates the microchip from the metal layer, the metal layer serves as a barrier to most liquids and vapors, and the outer parylene layer forms a more biocompatible interface with the surrounding environment (e.g. for implantable devices).

Other techniques one could use to conformally coat a microchip device include plating, spin coating, dip coating, and spraying. These may not be preferred, for example due to a need to cure certain coating material, the need to use solvents or heat, as well as the difficulty in achieving a truly conformal coating on devices having varied topography.

(b) Patterning of the Conformal Coating

In a preferred embodiment, the microchip is fabricated and the electrodes are masked. The microchip is then assembled to make the electrical connections, if necessary, for actively controlled microchips. The reservoirs can then be filled with molecules or devices. Parylene is then vapor deposited over the whole device and the masking covering the electrodes is removed. See FIG. 3, which illustrates these process steps. In another embodiment, the electrodes are not masked and parylene is selectively removed by a laser, plasma, or by another etching method after deposition.

It is possible that in another embodiment, a heated resistor or resistive material could be utilized to limit or prevent deposition of the coating material to selected areas of the microchip device—such as the reservoir caps. For example, a resistor or resistive material could be deposited under or near metal reservoir caps and etched away from the reservoirs. Parylene could then be deposited in two steps: First to the front of the substrate before reservoir filling and then to the back of the substrate after reservoir filling. The reservoir cap, such as a gold membrane, could be heated (e.g., to 150° C.) by applying a voltage to the resistors. If the heating can be controlled, it would prevent parylene from depositing on the reservoir cap. After assembling and filling, a second layer of parylene could be deposited onto only the back of the microchip, sealing the reservoirs and the package.

The methods described in U.S. Pat. Nos. 5,797,898 and 6,123,861, both to Santini et al., can be used to process the microchip devices prior to parylene coating. A mask may be used to protect the portion of the gold electrodes, which form the reservoir caps, from becoming coated with parylene. In a preferred embodiment, a physical mask, such as tape, can be positioned to cover the face of the microchip, or a coating such as photoresist or polyimide can be deposited and patterned over the electrodes. Parylene does not adhere well to gold, so the parylene can be readily removed, e.g., physically, if any is inadvertently deposited on the gold membrane surface.

If a physical mask is used to protect the reservoir barrier layers from parylene coating, then the parylene over the masked area can be removed, for example by cutting the mask away. If the microchip is not masked prior to the parylene deposition, then the microchip can be masked and the parylene removed by etching. One potential method of etching the parylene is by exposure to an oxygen plasma (i.e. oxygen is ionized under vacuum by RF power to create a plasma). The plasma reacts with the parylene to form carbon dioxide gas and water vapor, which are removed by the vacuum. The etching time is dependent upon the RF power and the temperature. An alternative method of etching parylene involves using a focused laser machining system. Most commercially available excimer lasers have relatively large beam sizes (e.g., 8×25 mm, 2×2 mm), and thus a mask would be required. The etching process would typically would involve the placement of a UV resistant mask above the microchip to define the area for the parylene to be removed. Then an excimer laser process would be used to remove parylene with high precision and sharp edge definition. Other types of lasers, such as a carbon dioxide laser, also could be used if they have sharp enough resolution to make the desired opening in the conformal coating.

To prepare the mask for selective removal from over the reservoir caps, one needs to define small windows in the masking material. In one embodiment, the steps for making such windows might include (1) evaporating or sputter coating the parylene film with a metal film such as aluminum or chromium; (2) coating the metal film with photoresist and patterning the resist with standard photolithographic methods to expose the metal in regions where the parylene windows will be formed; and (3) etching the exposed metal away using a suitable etchant. The parylene can then be removed with an oxygen plasma, which will also remove the remaining photoresist. The metal mask can then be removed by etching.

III. Functions and Uses of the Conformal Coatings

Both in vitro and in vivo applications of microchip delivery systems can benefit from conformal coatings. For example, the conformal coating can seal a drug in the reservoirs of a microchip without trapping air in the reservoirs, which can inhibit drug release. Conformal coating with parylene can also be applied to individually seal filled reservoirs, so that multiple drugs can be deposited and remain separated in a single microchip. In particular, the conformal coating advantageously seals electrical connections, so that the microchip device is electrically insulated from the fluid surrounding, or in contact with, the microchip. For in vivo applications, the conformal coating beneficially provides a biocompatible surface on the implanted device.

Sealing the Electrical Connections

For some active microchip devices, leads must be attached to the microchip to make electrical connections. This is accomplished by first attaching the microchip to a carrier such as a printed circuit board or plastic or ceramic carriers. Connections can then be made between the microchip and the carrier using wire bonds, as is commonly done in the integrated circuit industry. Additional wires can be attached to the carrier to make electrical connections to other circuits, components, carriers, or devices. In one embodiment, attachment of leads to the microchip can be carried out either before or after filling the reservoirs of the microchip with the drug or placing other materials or components in the reservoirs. In an alternative embodiment, a lead attachment method uses "flip chip" technology, which involves attaching the leads by reflowing solder bumps. Because this method involves the application of heat, it would have to be used before the microchip has been filled, in order to prevent damage to the drug or other components in the reservoirs. It is understood that one skilled in the art could use other standard integrated circuit packaging methods, as described, for example, in Lau & Lee, *Chip Scale Package* (McGraw-Hill, New York, N.Y. 1999).

Biocompatible Coatings

The microchip device desirably is provided with a biocompatible coating for implantation applications. Parylene can provide a biocompatible surface for implantation. Various manufacturers supplying coatings and coating equipment indicate that Parylene N and Parylene C have been tested for Acute Systemic Toxicity, Intracutaneous Toxicity and Implantation and are certified to comply with the USP biological testing requirements for classification VI (Specialty Coating Systems, Indianapolis, Ind., USA; see e.g., http://www.scscookson.com/applications/medical.htm). Parylene is not vulnerable to hydrolytic breakdown in an implantation environment because it has a polymeric backbone made up of carbon. Parylene C has been found to be compatible with living cells and cells will proliferate on coated surfaces. (Specialty Coating Systems, Indianapolis, Ind., USA; see e.g., http://www.scscookson.com/applications/medical.htm).

IV. Use of the Microchip Devices and Systems

The microchip device systems can be used in a wide variety of applications. The applications can be ex vivo or in vitro, but more preferably are for in vivo applications, particularly following non- or minimally-invasive implantation.

Preferred applications for using the devices and systems include the controlled delivery of a drug to sites within the body of a human or animal, biosensing, or a combination thereof. The microchip systems are especially useful for drug therapies in which it is desired to control the exact amount, rate, and/or time of delivery of the drug. Preferred drug delivery applications include the delivery of potent compounds, including both small and large molecules, such as hormones, steroids, chemotherapy medications, vaccines, gene delivery vectors, and some strong analgesic agents.

The microchips can be implanted into the body of a human or other animal via surgical procedures or injection, or swallowed, and can deliver many different drugs, at varying rates and varying times. In another embodiment, the microchip device includes one or more biosensors (which may be sealed in reservoirs until needed for use) that are capable of detecting and/or measuring signals within the body of a patient. As used herein, the term "biosensor" includes, but is not limited to, sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as blood gases, drug concentration, or temperature.

The system also has a variety uses that are not limited to implantation. For example, the reservoir contents may include a sensor for detecting a chemical or biological molecule at the site in which the microchip is placed, and the telemetry system transmits a status of the sensor detection to the remote controller. Such a site could be in vivo or in vitro. The chemical or biological molecule could, for example, be associated with a chemical or biological weapon, and the system used in an early warning/detection system.

Active microchip devices may be controlled by local microprocessors or remote control. Biosensor information may provide input to the controller to determine the time and type of activation automatically, with human intervention, or a combination thereof. The microchip devices have numerous in vivo, in vitro, and commercial diagnostic applications. The microchips are capable of delivering precisely metered quantities of molecules and thus are useful for in vitro applications, such as analytical chemistry and medical diagnostics, as well as biological applications such as the delivery of factors to cell cultures.

The invention can further be understood with reference to the following non-limiting examples.

EXAMPLE 1

Tape Masking and Parylene Coating a Microchip Device

Figure 3:
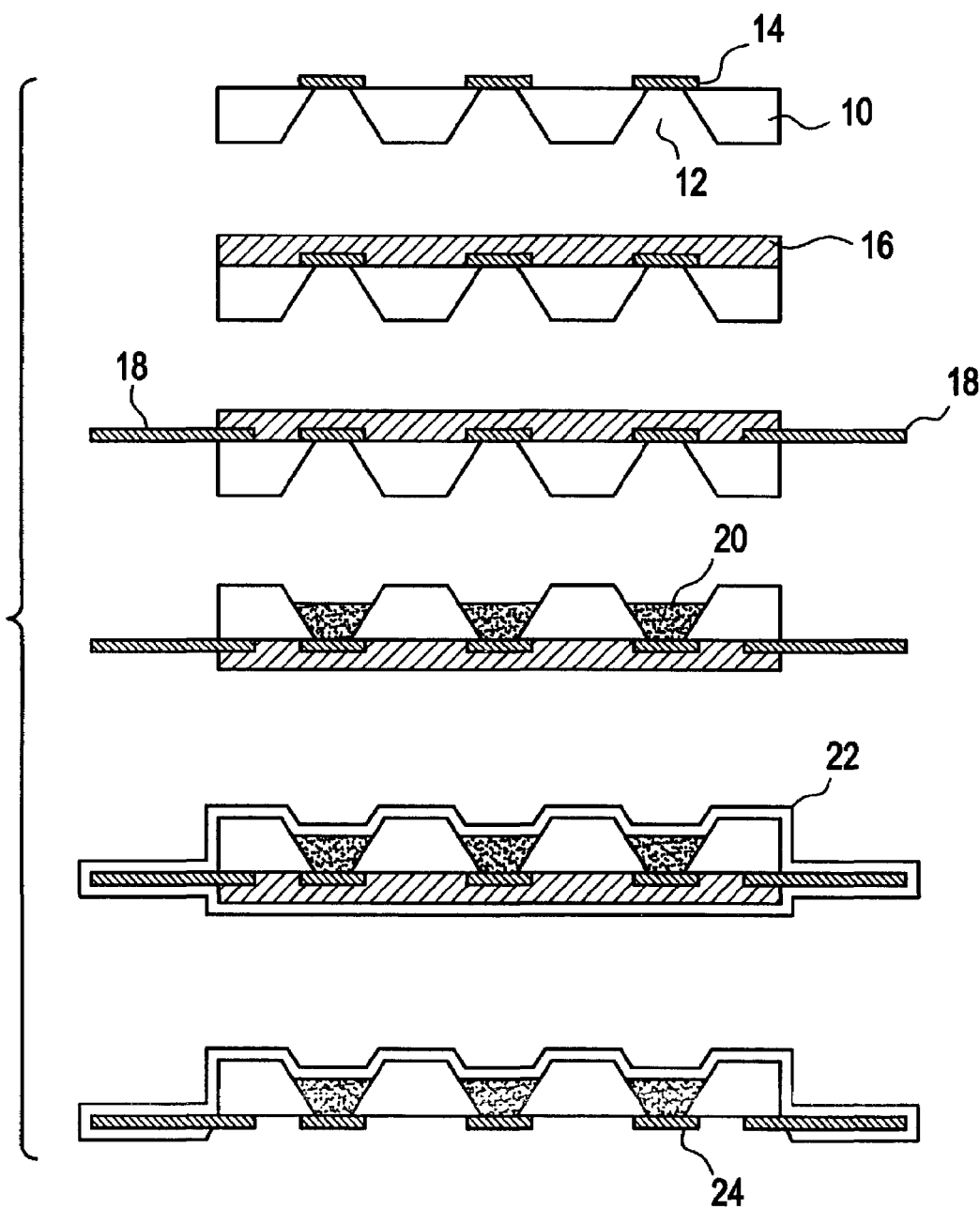
FIG. 3 illustrates, in cross-sectional views, one embodiment of a process for fabricated a conformally coated microchip device, wherein tape masking is used to pattern a parylene conformal coating.

This example is described with reference to FIG. 3. A microchip device substrate 10 with reservoirs 12 and gold membrane reservoir caps 14 were prepared using fabrication processes described in U.S. Pat. No. 6,123,861, to Santini, Jr. et al. The front of the microchip substrate, except for the wire bond pads, were masked with a water-soluble tape 16, 3M Mask Plus II Water Soluble Wave Solder Tape No. 5414. The tape 16 served to protect the microchip during assembly and to mask the front of the microchip during parylene coating. The microchip was attached to an assembly consisting of a cable soldered to a printed circuit board carrier (not shown). Connections 18 were made from the bond pads on the microchip to the bond pads on the board using a wire bonder. In this experiment, these wire bonds were protected with epoxy so the microchip could be turned over and leads could be soldered to the back of the printed circuit board. (In actual practice, the parylene or other conformal coating, rather than epoxy, would protect and insulate the wire bonds, if wire bonds were to be used.) The microchip was then filled with a drug 20. The assembled device was then coated in a layer of vapor deposited parylene 22, including the wire bonds and the solder joints. The parylene was scored around the edge of the tape 16, and the tape was removed. Finally, the microchip was soaked in water to remove the water-soluble adhesive from the face of the microchip, leaving exposed reservoir caps 24.

EXAMPLE 2

Parylene Coating Followed by Selective Laser Removal

Figure 4:
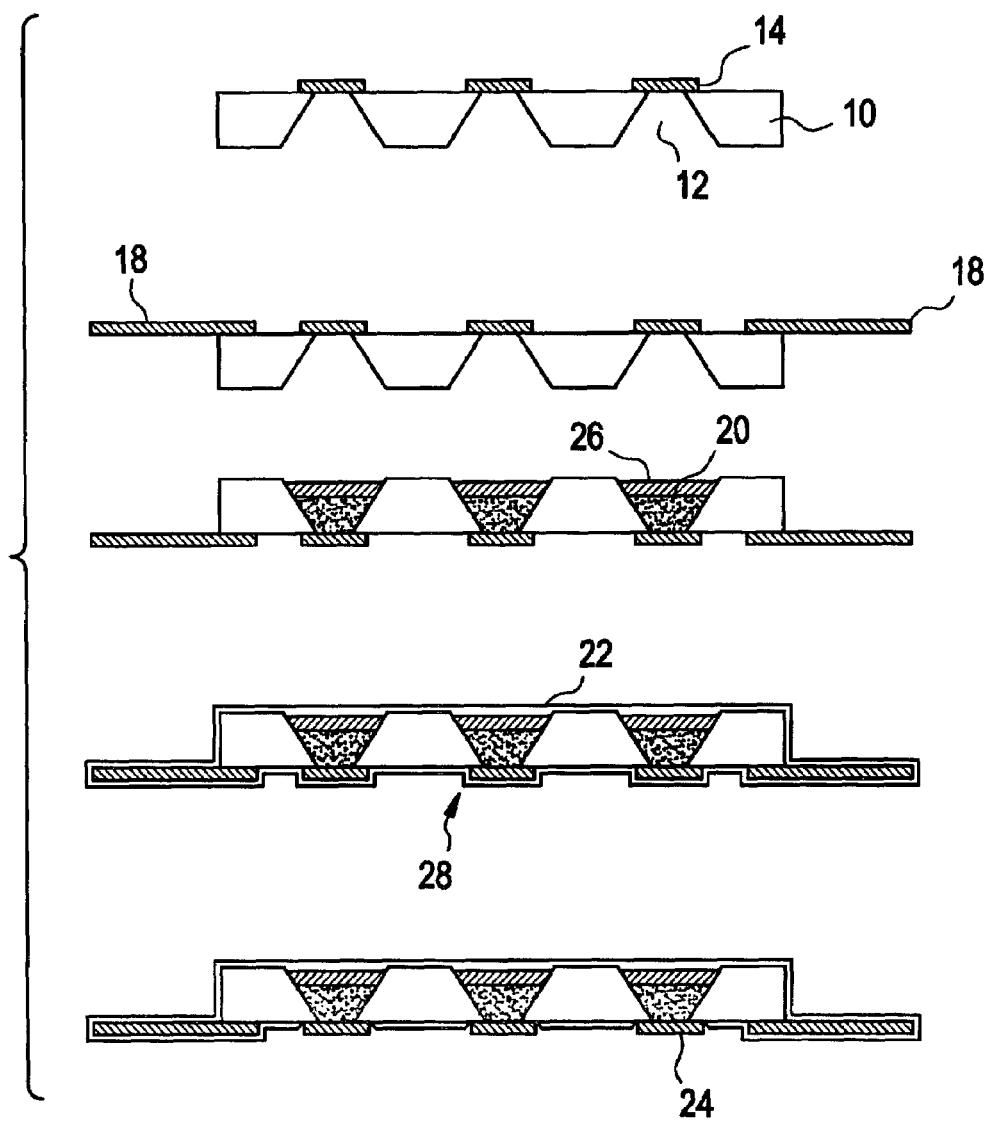
FIG. 4 illustrates, in cross-sectional views, one embodiment of a process for fabricated a conformally coated microchip device, wherein an excimer laser is used to remove the coating over the reservoir caps.

This example is described with reference to FIG. 4. The microchip device substrate 10 with reservoirs 12 and gold membrane reservoir caps 14 would be manufactured and mounted to a flexible-circuit carrier as described in Example 1. The connections 18 would be made by wirebonding the microchip bond pads to the exposed leads on the flex circuit. The wirebonds would be protected during reservoir filling. The reservoirs 12 would then filled with a drug 20, and then a wax layer 26 would then added to fill the remaining volume of the reservoirs 12 over the drug 20 before sealing the reservoirs 12 of the device. The entire microchip device package would then conformally coated with parylene 22, consequently sealing reservoirs 12. A contact mask (not shown), which would be made of a metal or another excimer laser-resistant material, would then be placed over the face 28 of the parylene-coated microchip device. A laser would then be directed to selectively ablate the parylene or to cut the parylene around the edges of the reservoir caps to expose the reservoir caps 24.

EXAMPLE 3

Improved Barrier Properties with a Metal Film

Figure 5:
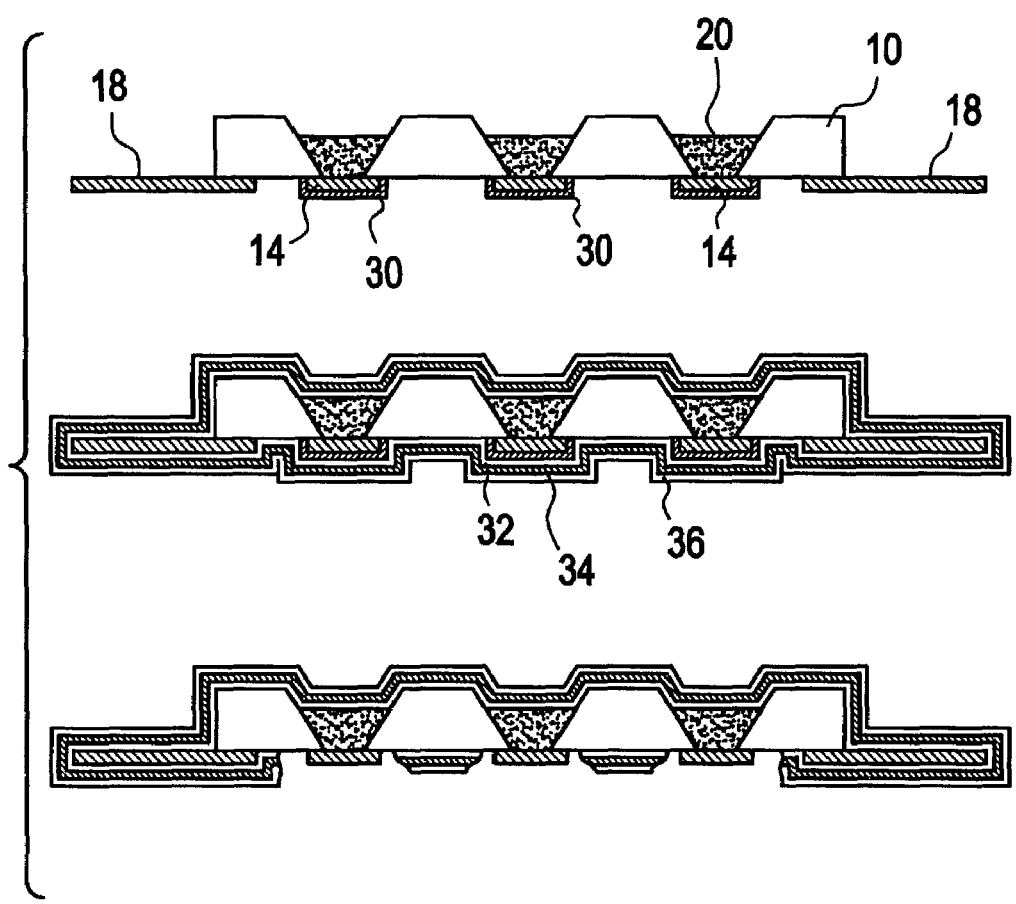
FIG. 5 illustrates, in cross-sectional views, one embodiment of a process for fabricated a conformally coated microchip device, wherein the conformal coating includes a metal layer interposed between two layers of parylene.

This example is described with reference to FIG. 5. The microchip device substrate 10 with reservoirs 12 and gold membrane reservoir caps 14 would be manufactured as described in Example 1. This microchip device substrate would then be mounted to a package that has solder bumps placed in a pattern that matches the bond pads on the microchip. The microchip and package would then be brought into contact with each other and the solder bumps heated so they reflow and make electrical connection. The reservoir caps 14 would then be masked. Then the reservoirs would be filled with a drug 20. Next, a first layer 32 of parylene would be conformally coated onto the assembled microchip device. Then a layer of metal film 34, such as aluminum, would be evaporated or sputtered over first parylene layer 32 to form an impermeable barrier. An outer layer 36 of parylene would then be conformally coated over the metal film 32 to provide a biocompatible outer layer for the microchip device. The mask 30 would then be removed. If a masking tape were to be used, then the parylene/metal layers (32/34/36) would first be scored to facilitate separation only over the reservoir caps 14, leaving the remaining coating structure intact.

This laminate structure approach also could be used to seal the reservoir openings (distal the reservoir caps) after the reservoirs are filled with the drug. If needed, a buffer layer, such as the wax layer described in Example 2, could be included. Then the back side of the substrate would be coated with parylene or another vapor depositable coating material. Using a patterning method, such as masked plasma etching, the parylene would be selectively removed from the backside surfaces between the reservoirs. Then a metal film would be deposited to coat the parylene over the drug and the substrate between the reservoirs. A second coat of parylene would then be deposited over the metal film. This approach provides a barrier between the reservoirs, so that once the drug is released from a reservoir and the opened reservoir becomes filled with fluid (e.g., bodily fluids), the metal film reduces the vapor transmission to adjacent reservoirs.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method for sealing reservoirs containing molecules or devices in a microchip device, the method comprising:
    providing a substrate having a plurality of reservoirs, a front side, and a back side, the back side comprising a plurality of reservoir openings distal reservoir caps on the front side and in need of sealing;
    loading reservoir contents comprising molecules, a secondary device, or both, into the reservoirs;
    applying a buffering material over the reservoir contents in the reservoirs, the buffering material being discontinuous between the reservoirs; and
    applying a conformal coating barrier layer onto the buffering material, wherein the conformal coating barrier layer is applied by vapor deposition, plating, spin coating, or multi-laminate coating.

2. The method of claim 1, further comprising removing the conformal coating from the reservoir caps.

3. The method of claim 2, wherein the removal is by chemical or plasma etching or by laser.

4. The method of claim 1, wherein the conformal coating is a uniform, bubble-free, pinhole-free coating.

5. The method of claim 1, wherein the conformal coating barrier layer comprises parylene.

6. The method of claim 1, wherein the conformal coating comprises a material selected from the group consisting of acrylics, polyurethanes, silicones, and combinations thereof.

7. The method of claim 1, wherein the buffering material comprises a wax or polymer.

8. The method of claim 1, wherein the reservoirs contents comprises drug molecules for controlled release.

9. The method of claim 1, wherein the reservoirs contents comprises a sensor or sensing component.

10. The method of claim 9, wherein the reservoir contents comprises a biosensor.

11. The method of claim 1, wherein the conformal coating barrier layer comprises a polymer and a metal.

12. The method of claim 1, wherein the conformal coating barrier layer has a thickness between 0.1 and 50 microns.

* * * * *